(12) United States Patent
Alzona et al.

(10) Patent No.: US 10,183,488 B2
(45) Date of Patent: Jan. 22, 2019

(54) PRINTER FLUID IMPEDANCE SENSING IN A PRINTHEAD

(71) Applicant: HEWLETT-PACKARD DEVELOPMENT COMPANY, L.P., Houston, TX (US)

(72) Inventors: Gerard Alzona, San Diego, CA (US); David Maxfield, Philomath, OR (US); Dustin W Blair, Escondido, CA (US); Sterling Chaffins, Corvallis, OR (US); Andrew L Van Brocklin, Corvallis, OR (US)

(73) Assignee: HEWLETT-PACKARD DEVELOPMENT COMPANY, L.P., Houston, TX (US)

( * ) Notice: Subject to any disclaimer, the term of this patent is extended or adjusted under 35 U.S.C. 154(b) by 0 days.

(21) Appl. No.: 15/547,393

(22) PCT Filed: Apr. 30, 2015

(86) PCT No.: PCT/US2015/028611
§ 371 (c)(1),
(2) Date: Jul. 28, 2017

(87) PCT Pub. No.: WO2016/175853
PCT Pub. Date: Nov. 3, 2016

(65) Prior Publication Data
US 2018/0022091 A1    Jan. 25, 2018

(51) Int. Cl.
*B41J 2/14* (2006.01)
*B41J 2/045* (2006.01)
(Continued)

(52) U.S. Cl.
CPC ............ *B41J 2/125* (2013.01); *B41J 2/0451* (2013.01); *B41J 2/0458* (2013.01);
(Continued)

(58) Field of Classification Search
CPC .... B41J 2/0451; B41J 2/04555; B41J 2/0458; B41J 2/04581; B41J 2/11; B41J 2/125;
(Continued)

(56) References Cited

U.S. PATENT DOCUMENTS 4,872,028 A    10/1989   Lloyd
5,418,558 A     5/1995   Hock et al.
(Continued)

FOREIGN PATENT DOCUMENTS

CN    104080609        10/2014
CN    104080610 A      10/2014
(Continued)

OTHER PUBLICATIONS

Sen, et al. Droplet Ejection Performance of a Monolithic Thermal Inkjet Print Head. Jun. 21, 2007.

*Primary Examiner* — Anh T. N. Vo
(74) *Attorney, Agent, or Firm* — HP Inc.—Patent Department

(57) ABSTRACT

In some examples, a printhead includes a firing chamber to receive printer fluid, an ejector positioned in the firing chamber to eject printer fluid droplets from the printhead, and a nozzle in fluid communication with the firing chamber. The printhead can further include an impedance sensor positioned in the firing chamber to contact printer fluid to measure impedance values of the printer fluid. The impedance sensor can be connectable to a controller to transmit impedance values of printer fluid to the controller.

20 Claims, 6 Drawing Sheets

(51) Int. Cl.
*B41J 2/125* (2006.01)
*B41J 29/13* (2006.01)
*G01N 27/10* (2006.01)
*B41J 2/11* (2006.01)

(52) U.S. Cl.
CPC ....... *B41J 2/04536* (2013.01); *B41J 2/04555* (2013.01); *B41J 2/04581* (2013.01); *B41J 2/14153* (2013.01); *B41J 2/14201* (2013.01); *B41J 29/13* (2013.01); *B41J 2/11* (2013.01); *B41J 2002/14354* (2013.01); *G01N 27/10* (2013.01)

(58) Field of Classification Search
CPC .. B41J 2/14153; B41J 2/14201; B41J 2/2142; B41J 2002/14354; G01N 27/10
See application file for complete search history.

(56) References Cited

U.S. PATENT DOCUMENTS

| | | | |
|---|---|---|---|
| 6,354,687 B1 | 3/2002 | Su et al. | |
| 6,685,290 B1 * | 2/2004 | Farr | B41J 2/17546 347/7 |
| 6,929,343 B2 * | 8/2005 | Farr | B41J 2/17566 347/19 |
| 7,510,259 B2 | 3/2009 | Geer | |
| 7,735,945 B1 * | 6/2010 | Sliwa, Jr. | B41J 2/04 347/14 |
| 7,988,265 B2 * | 8/2011 | Smith | B41J 2/1707 347/84 |
| 2003/0142159 A1 | 7/2003 | Askeland et al. | |
| 2005/0001863 A1 | 1/2005 | Farr et al. | |
| 2006/0170744 A1 | 8/2006 | Boesten et al. | |
| 2013/0278656 A1 | 10/2013 | Govyadinov et al. | |
| 2014/0078228 A1 | 3/2014 | Kataniwa | |
| 2014/0210881 A1 | 7/2014 | Van Brocklin et al. | |
| 2015/0124011 A1 | 5/2015 | Van Brocklin | |

FOREIGN PATENT DOCUMENTS

| | | |
|---|---|---|
| CN | 104169091 | 11/2014 |
| WO | WO 2016085471 A1 | 6/2016 |

\* cited by examiner

PRINTER FLUID IMPEDANCE SENSING IN A PRINTHEAD

BACKGROUND

Inkjet printers can be used to print text, pictures, or other graphics by propelling droplets of printing fluid onto paper or other printer media. Such printers can include one or more printing fluid reservoirs to feed printer fluid to one or more printheads. Such reservoirs can contain different kinds of printing fluids, such as different colored printing fluids, so as to allow the printer to print graphics in monochrome as well as color.

BRIEF DESCRIPTION OF THE DRAWINGS

For a detailed description of various examples, reference will now be made to the accompanying drawings in which.

NOTATION AND NOMENCLATURE

Figure 1:
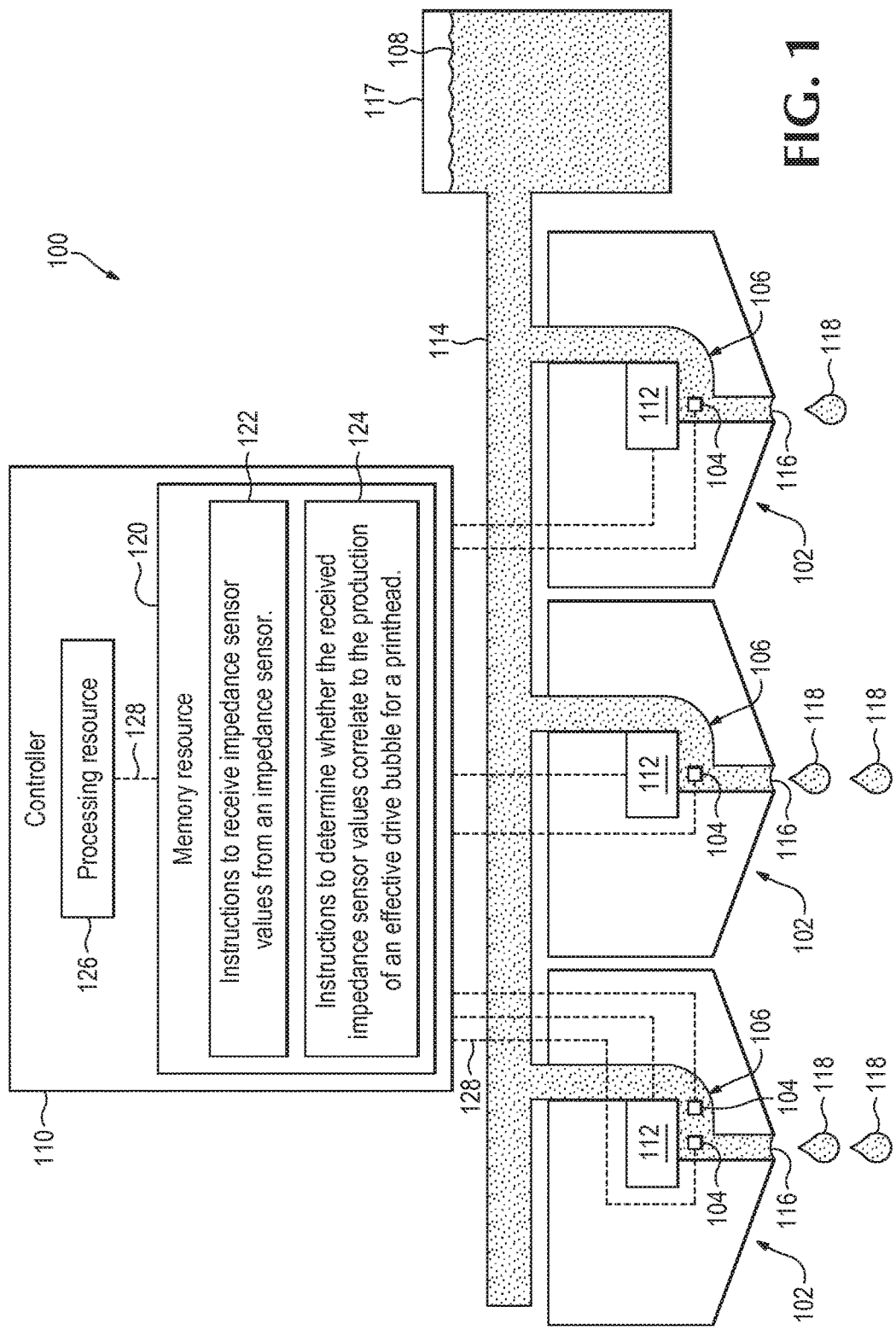
FIG. 1 is a diagram of a system, according to an example.

The following discussion is directed to various examples of the disclosure. Although one or more of these examples may be preferred, the examples disclosed should not be interpreted, or otherwise used, as limiting the scope of the disclosure, including the claims. In addition, the following description has broad application, and the discussion of any example is meant only to be descriptive of that example, and not intended to intimate that the scope of the disclosure, including the claims, is limited to that example. For example, in the following discussion and in the claims, the terms "including" and "comprising" are used in an open-ended fashion, and thus should be interpreted to mean "including, but not limited to . . . ."

DETAILED DESCRIPTION

Various components of printheads can degrade over time and can result in changes in printhead output, accuracy, quality, efficiency, etc. In particular, an energy used to eject a healthy printer fluid droplet out of a printhead nozzle can change as printhead ejectors (e.g., certain thermal inkjet (TIJ) resistor heaters, piezoelectric inkjet (NJ) mechanical actuators, etc.) degrade over time. As an example for certain TIJ printheads, during normal firing, energy can be delivered to an ejector, which heats up the ejector to create a drive bubble that pushes ink out of the printhead nozzle. In such a printhead, the efficiency of the heater ejector can degrade over time, which can result in greater current being applied to the heater in order to form an effective drive bubble.

The present disclosure is directed to improved systems, printheads, printhead controllers, etc., that can, in some implementations, allow for real-time drop ejection effectiveness evaluation during printing, which can, in some implementations, enable turn on energy optimization without loss of productivity. For example, in some implementations, an impedance of printer fluid in contact with an impedance sensor can be measured, which can allow the system to detect if an effective drive bubble has been created. In some implementations, a nucleation threshold (e.g., a point at which drop ejection starts to occur), as well as other stages in drive bubble formation or other printhead properties can be detected by such a system. An example implementation of such a system (which is described in further detail below) can, for example, include an impedance sensor positioned in a firing chamber of a printhead to contact printer fluid to measure impedance values of the printer fluid. The system can further include a printhead controller to receive impedance sensor values from the impedance sensor and determine whether the received impedance sensor values correlate to the production of an effective drive bubble for the printhead.

Certain implementations of the present disclosure can exhibit advantages compared to existing techniques of using simulated environments to predict printhead component degradation over time as well. For example, in some implementations, real-time detection can be provided, which can reduce or eliminate loss in productivity or imprecision in predictive modeling, which can in some situations result from normal variations in manufactured components causing deviations from nominal modelled behavior. Likewise, certain implementations of the present disclosure can provide for adaptive nozzle recovery, which can, for example, allow for aggressive firing parameters for resistor plate cleaning and normal operation when cleaning is complete. In some implementations, the present disclosure can be used to significantly extend the useful life of a printhead by optimizing energy over the life of the device. Other advantages of implementations presented herein will be apparent upon review of the description and figures.

FIG. 1 is a diagram of an example implementation of a system 100 that can, for example, be used to measure impedance values of printer fluid within a printhead. As described in further detail below, system 100 can, for example, include a printhead 102 including an impedance sensor 104 positioned in a firing chamber 106 of printhead 102 to contact printer fluid 108 to measure impedance values of printer fluid 108. As described in further detail below, system 100 can further include a printhead controller 110 to receive impedance sensor values from impedance sensor 104 and determine whether the received impedance sensor values correlate to the production of an effective drive bubble for printhead 102. The structure and functionality of these components and others will be described in further detail below.

Figure 3:
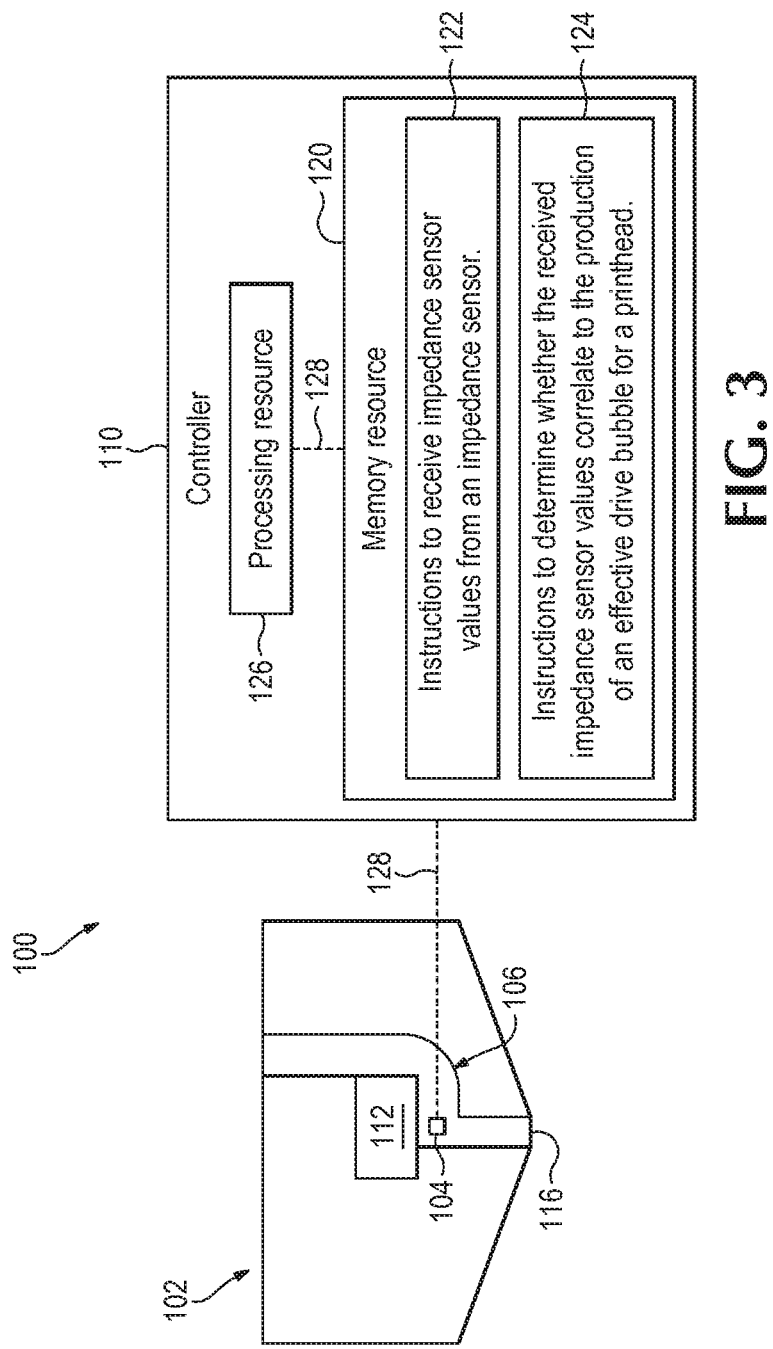
FIG. 3 is a diagram of a system, according to another example.

In the implementation illustrated in FIG. 1, system 100 includes multiple printheads 102 with respective firing chambers 106 and other printhead components to allow independent ejection of printer fluid 108. However, it is appreciated that other implementations are envisioned in the present disclosure. For example, and as described in further detail below, FIG. 3 illustrates an example system 100 including only a single printhead 102 and controller 110.

The term "print", "printer", and the like, as used herein can, for example, refer to both machines capability of printing or otherwise precisely depositing materials on a substrate (e.g., for certain medical applications). For example, the term "printer" as used herein can refer to an all-in-one device that provides printing as well as non-printing functionality, such as a combination printer, three-dimensional (3D) printer, scanner, and fax machine. One implementation of a suitable printer for use with the system described herein is shown in FIG. 1 and is described in further detail below. In addition, the term "print" can, for example, refer to any suitable technique, such as ejecting, spraying, propelling, depositing, or the like. With respect to 3D printers, printhead 102 can be a 3D print fluid printhead, a 3D agent printhead, a pharmaceutical digital drop dispenser, or any other suitable high precision digital drop dispenser.

The industry term "inkjet" is used for convenience and is not intended to refer to only ink-based printers. That is, the term "inkjet printhead," can refer to a printhead that uses any suitable printer fluid. The term "printer fluid" as used herein can, for example, refer to printer ink as well as suitable non-ink fluids. For example, printer fluid can include a pre-conditioner, gloss, a curing agent, colored inks, grey ink, black ink, metallic ink, optimizers, bio-fluids, and the like. Suitable inks for use in inkjet printers can, for example, be water based inks, latex inks or the like. In some implementations, printer fluid can be in the form of aqueous or solvent printing fluid and can be any suitable color, such as black, cyan, magenta, yellow, etc. In some implementations, printer fluid can include functional fluids, such as for example pre-treatment fluids for adhesion and/or post-treatment fluids or overcoats for durability.

The term "printer media" as used herein can, for example, refer to any form of media onto which system 100 is designed to print. For example, printer media can be in the form of computer paper, photographic paper, a paper envelope, or similar paper media. Such printer media can be a standard rectangular paper size, such as letter, A4 or 11×17. It is appreciated that printer media can in some implementations be in the form of suitable non-rectangular and/or non-paper media, such as clothing, wood, or other suitable materials. For example, in some implementations, the term "printer media" as used herein can refer to a bed of build material for use in 3D printing.

Printhead 102 includes firing chamber 106 to receive printer fluid 108. Firing chamber 106 can, for example, house an ejector 112, impedance sensor 104 and can be used to receive printer fluid from fluid line 114 for ejection from printhead 102. Fluid line 114 can be in the form of a manifold, fluid slot, fluid hole array, either delivering to individual printheads 102 or to groups of printheads 102. In some implementations, fluid line 114 is not part of printhead 102 itself. Instead, for example, fluid line 114 can be part of packaging or other structure.

Printhead 102 includes nozzle 116 in fluid communication with firing chamber 106. Nozzle 116 can be designed to control a direction or characteristics of printer fluid flow as it exits printhead 102. For example, nozzle 116 can be designed to control the rate of flow, speed, direction, mass, shape, and/or the pressure of the stream that emerges from them. As described in further detail below, in some implementations of system 100, printer media can, during printing, be moved under nozzle 116 of printhead 102. And printhead 102 can be designed to print text, pictures, or other graphics onto the printer media by propelling droplets of liquid printing fluid through nozzle 116 and onto the printer media. In some implementations, nozzle 116 can be a separate piece removably attached to printhead 102 such that a single channel is formed through printhead 102 and nozzle 116. In some implementations, nozzle 116 is a single piece of material with printhead 102 and may alternatively be referred to as a nozzle portion of printhead 102.

Printhead 102 includes an ejector 112 positioned in firing chamber 106 to eject printer fluid droplets 118 from printhead 102. Ejector 112 of printhead 102 can be designed to print printer fluid 108 onto printer media. Printhead 102 can, for example, be designed to print via a thermal inkjet process. For example, in certain thermal inkjet processes, printing fluid droplets are ejected from a printhead 102 via a pulse of current that is passed through an ejector 112 in the form of a heater positioned in firing chamber 106 of printhead 102. Heat from the heater causes a rapid vaporization of printing fluid in printhead 102 to form a drive bubble, which causes a large pressure increase that propels a droplet 118 of printing fluid onto the printer media. In some implementations, printhead 102 can be designed to print via a piezoelectric inkjet process. In certain piezoelectric inkjet processes, a voltage is applied to an ejector 112 in the form of a piezoelectric material located in firing chamber 106 of printhead 102. When a voltage is applied, the piezoelectric material changes shape, which generates a pressure pulse that forces a droplet 118 of printing fluid from printhead 102 onto printer the media. It is appreciated that other forms of ejector 112 and other types of printheads can be used in accordance with the present disclosure.

Printhead 302 includes impedance sensor 104 positioned in firing chamber 106 to contact printer fluid 108 to measure impedance values of printer fluid 108. Impedance measurements of printer fluids can be based on chemical properties of the printer fluid as well as certain environmental properties. Impedance sensor 104 can be designed to generate an electrical signal as a function of the impedance of the printer fluid. For example, an analog signal can be read from impedance sensor 104 and healthy and weak drop ejection can be distinguished, as described in further detail herein. In some implementations, impedance sensor 104 is able to measure impedance values between a sensor and substrate (e.g., printer fluid 108 or another substrate) or between two sensors. It is appreciated that any suitable form of impedance sensor 104 may be used. For example, in certain implementations, such as certain piezoelectric (or other) inkjet implementations, impedance sensor 104 can be used to determine properties of printhead 102 based on multiple types of bubble sources, such as for example air ingestion or gases coming out of solution (e.g., due to heating of the fluid). That is, in some implementations, impedance sensor 104 is to measure impedance values correlated to determining the need for servicing due to air accumulation, deposits, contamination, or other degradation.

In some implementations, impedance sensor 104 can, for example, be constructed of two electrodes that allow fluid impedance to be measured between the two electrodes. In some implementations, respective conductive surfaces of the two electrodes can be directly in contact with the fluid, whereas in some implementations, the respective conductive surfaces of the electrodes can be separated from the fluid by an insulator or other suitable material. Such an insulator can, for example, be a native oxide of the conductor, such as Tantalum Pentoxide grown by oxidation on a Tantalum electrode. In some implementations, the insulator can, for example, be a deposited material such as Silicon Dioxide or PDMS on a conductor such as Aluminum, Copper, Tantalum, Gold or alloys thereof. In some implementations, sensor electrodes of impedance sensor 104 can, for example, be in pairs, with one pair per sensor. Such a configuration may rely on extra circuitry or at least extra electrical connections in printhead 102 compared to using a common electrode. To reduce the overhead for providing such impedance sensing device in an array on a printhead 102, a common electrode scheme can be used. In such an implementation, one electrode of impedance sensor 104 could be in an inkjet nozzle structure, while another could be a large common structure that acts as a second electrode for all or some of the electrodes on inkjet printhead 102.

Impedance measurements can, for example, be current driven or voltage driven. In the case of voltage drive, a pulse wave or other wave-shape such a sinusoidal voltage is driven onto the plate, and the current that moves between the two plates is sensed. The current drive can be complementary to the voltage drive described, in that a current wave-shape can be driven and the voltage between the plates can be sensed.

For bubble absence or presence detection, impedance sensor 104 may rely on a simple wave-shape, such as a current pulse, and monitoring a measurement of the voltage present at some time point during or after a current pulse. In some situations and implementations, this can provide sufficient sensor information output for the application and may be less costly in terms of circuitry. For other applications, such as where build up is being detected for example, a more comprehensive impedance measurement may be used. For example, in some implementations, an impedance spectroscopy could be used. One or more suitable variations of impedance spectroscopy may be used, such as using a multiple frequency sequential sinusoidal drive and sensing the magnitude and phase of the resulting output. The frequencies used for the stimulus can, for example, be based on desired characteristics being sensed and what amount of information is used.

It is appreciated that other impedance sensing techniques may be used, such as for example a bridge or network, where the output of the whole is measured. It is further appreciated that the above description of impedance sensor 104 is intended to only describe typical methods, and does not limit the techniques used for sensing fluid impedance. For example, in some implementations, electrochemical impedance spectroscopy may be used for impedance measurements.

In some implementations, such as that shown in FIG. 1, impedance sensor 104 is in electronic communication with a controller, such as controller 110, which can, in some implementations, allow advanced processing of impedance sensor measurements and control of printhead 102 based on such measurements. In the implementation of system 100 of FIG. 1, each firing chamber 106 of each printhead 102 includes one or two impedance sensors 104. However, it is appreciated that in some implementations, impedance sensors 104 are only present in a subset of printheads 102 (e.g., all but one printhead, only one printhead, etc.) or only a subset of nozzles 116 on a given printhead.

Reservoir 117 is designed to store a supply of printer fluid 108 for use in system 100. Reservoir 117 can be in a form suitable for long-term storage, shipment, or other handling. Reservoir 117 can, for example, be a rigid container with a fixed volume (e.g., a rigid housing), a deformable container (e.g., a deformable bag), or any other suitable container for the printing fluid supply. Reservoir 117 can be stored within a housing of system 100. For example, in some implementations, a cover or housing panel of a printer can be removed to allow a user to access and/or replace reservoir 117. In some implementations, reservoir 117 can be located outside of a housing of system 100 and can, for example, be fluidly connected to system 100 via an intake port on an exterior surface of a housing of system 100.

Printer fluid 108 can be flowed from printing fluid reservoir 117 to printhead 102 via a pump, plunger, or another suitable actuator. For example, in implementations where reservoir 117 is a flexible bag, an actuator can be used to compress reservoir 117 to force printer fluid 108 out of reservoir 117 and into printhead 102 or an intermediary fluid path connecting reservoir 117 and printhead 102. In some implementations, reservoir 117 can be positioned above printhead 102 so as to allow a gravitational force to assist in providing printer fluid 108 from reservoir 117 to printhead 102. Although reference is made herein to printer fluid 108 being transferred from reservoir 117 to printhead 102, it is appreciated that in some implementations, system 100 can be designed to flow printer fluid 108 from printhead 102 to reservoir 117 for storage or another desired purpose.

Printhead 102 includes printhead controller 110 in data communication with impedance sensor 104 via one or more communication links 128. Controller 110 can, for example, signal to each ejector 112 of each printhead 102 to eject printer fluid 108 through its respective nozzle 116. Printhead controller 110 can include a memory resource 120 that stores various machine readable instructions 122 and 124 (described below) to cause a processing resource 126 to perform various operations.

Instructions 122 are to cause processing resource 126 to receive impedance sensor values from impedance sensor 104. As provided above, in some implementations, an analog signal can be read from impedance sensor 104. The impedance values can be transmitted to processing resource 126 in real-time and/or can be stored on impedance sensor 104 for delayed transmission to controller 110. In some implementations, instructions 122 can be in the form of firmware or other instructions to convert signals or other transmission data from impedance sensor 104 into readable values associated with impedance sensor measurements.

Instructions 124 can be stored on a memory resource 120 of controller 110 to cause processing resource 126 to determine whether the received impedance sensor values correlate to the production of an effective drive bubble for printhead 102. For example, impedance sensor values can be used to identify various stages of a drive bubble formation throughout a firing event, such as achieving a nucleation threshold. In some implementations, instructions 124 can include instructions to determine, based on impedance sensor values, whether nozzle 116 is blocked with printer fluid 108 or other material. It is appreciated that instructions 124 can include instructions to compare the received impedance values to data for effective drive bubble production for the same model of printhead 102 for a specific type of printer fluid 108. The data used in such an operation can, for example, be acquired from predictive modeling for the same printhead or another printhead and/or can, for example, be acquired from historical or experimental data.

In some implementations, instructions 124 can include instructions to trigger a printhead servicing operation for printhead 102 based on the received impedance sensor values. For example, certain impedance measurements can be correlated to degraded performance of printhead 102. It is appreciated that the trigging of a servicing operation can be in addition to other actions based on the received impedance sensor values. For example, when a threshold level of degradation is determined, a printhead servicing operation can be triggered and a new measurement of firing energy can be applied to subsequent operation. In such an implementations, servicing repeats can be be initiated if printhead 102 is not subsequently determined to be at least partially recovered by initial servicing operation.

In some implementations, instructions 124 are to determine correlations based on whether impedance sensor measurements are within a predetermined range of values. It is appreciated that the predetermined range of values can be calculated dependent on aspects of system 100, e.g., a size of firing chamber 106, local or environmental temperature, material properties of printer fluid 108, and/or other aspects of printhead 102 or a printing environment.

Suitable processing resources 126 for use with controller 110 can, for example, be in the form of a central processing unit (CPU), a semiconductor-based microprocessing resource, a digital signal processing resource (DSP) such as a digital image processing unit, other hardware devices or processing elements suitable to retrieve and execute instructions stored in a computer-readable medium, or suitable combinations thereof. Suitable processing resources can, for example, include single or multiple cores on a chip, multiple cores across multiple chips, multiple cores across multiple devices, or suitable combinations thereof. Suitable processing resources can be functional to fetch, decode, and execute instructions as described herein. As an alternative or in addition to retrieving and executing instructions, suitable processing resources can, for example, include at least one integrated circuit (IC), other control logic, other electronic circuits, or suitable combination thereof that include a number of electronic components for performing the functionality of instructions stored on a computer-readable medium. Suitable processing resources 126 can, for example, be implemented across multiple processing units and instructions may be implemented by different processing units in different areas of controller 110.

As provided above, printhead controller 110 includes memory resource 120 that stores machine readable instructions 122 and 124. Suitable memory resources 120 of controller 110 can include any machine-readable storage medium for use by or in connection with an instruction execution system such as a computer/processor based system or an ASIC (Application Specific Integrated Circuit) or other system that can fetch or obtain the logic from computer-readable medium and execute the instructions contained therein. Suitable machine-readable storage mediums can, for example, be in the form of non-transitory storage mediums. The term "non-transitory" as used herein can, for example, refer to mediums that do not encompass a transitory signal but instead are made up of one or more memory resource components configured to store relevant machine-readable instructions. Such mediums can, for example, be in the form of electronic, magnetic, optical, or other physical storage mediums to store information, such as computer instructions.

As used herein, the term "machine-readable storage medium" can, for example, include Random Access Memory resource (RAM), flash memory resource, a storage drive (e.g., a hard disk), any type of storage disc (e.g., a Compact Disc Read Only Memory resource (CD-ROM), any other type of compact disc, a DVD, etc.), and the like, or a combination thereof. In some implementations, mediums can correspond to a memory resource including a main memory resource, such as a Random Access Memory resource (RAM), where software may reside during runtime, and a secondary memory resource. The secondary memory resource can, for example, include a nonvolatile memory resource where a copy of machine-readable instructions are stored. It is appreciated that instructions and data can be stored on separate machine-readable storage mediums. For purposes of clarity, multiple memory resources can be identified as a single memory resource and multiple processing resources can be identified as a single processing resource.

Memory resource 120 can be in communication with processing resource 126 via a communication link 128. Communication link 128 between processing resource 126 and memory resource 120 (as well as communication link 128 between printheads 102 and controller 110) can be local or remote to a machine (e.g., a computing device) associated with processing resource 126. Examples of a local communication link 128 can include an electronic bus internal to a machine (e.g., a computing device) where memory resource 120 is one of volatile, non-volatile, fixed, and/or removable storage medium in communication with processing resource 126 via the electronic bus.

In some implementations, controller 110 can control alternative or additional aspects of system 100. It is appreciated that the various components of controller 110 can be housed within a common housing or can be in separate housings connected via one or more signal paths. As another example, in some implementations, memory resource 120 of controller 110 and/or processing resource 126 of controller 110 can be in a separate housing external of a computing device connected to system 100 via a plug or another signal path.

Figure 2:
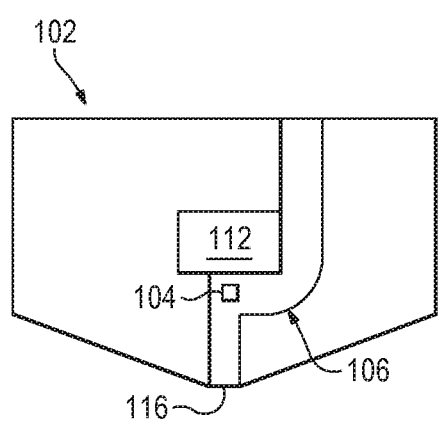
FIG. 2 is a diagram of a printhead, according to an example.

FIG. 2 is a diagram of an example printhead 102 by itself. For convenience, printhead 102 of FIG. 2 includes the same reference numerals as that illustrated and described above with respect to system 100 of FIG. 1. Unlike the diagram of system 100 of FIG. 1, which is intended to depict a portion of a system ready for operation on site, the diagram of printhead 102 of FIG. 2 is intended to illustrate only a subset of components that might be included in a commercial product sold as a printhead. For example, it is appreciated that some printheads are not sold along with printer fluid or with printhead controllers. Moreover, it is appreciated that printhead 102 of FIG. 2 can include additional, fewer, or alternative components or functionality as system 100 of FIG. 1 and/or can be modified or assembled to include additional components, functionality, etc. Moreover, various aspects of system 100 of FIG. 1 can be incorporated into printhead 102 of FIG. 2 and vice versa. As an example, printhead 102 of FIG. 2 can include communication links 128 (as shown for example in system 100 of FIG. 1) for connecting to a controller, such as controller 110. In addition, it is appreciated that printhead 102 may include other aspects, such as various sensors, printer fluid lines, structural supports, etc. that are intentionally omitted in the simplified printhead diagram of FIG. 2.

Similar to printhead 102 illustrated in FIG. 1, printhead 102 of FIG. 2 can include firing chamber 106 to receive printer fluid (not shown in FIG. 2, but labelled as printer fluid 108 in FIG. 1), ejector 112 positioned in firing chamber 106 to eject printer fluid droplets 118 from printhead 102, and nozzle 116 in fluid communication with firing chamber 106. Similar to nozzle 116 of system 100 of FIG. 1, nozzle 116 of printhead 102 of FIG. 2 can, for example, be designed to direct printer fluid droplets (not shown in FIG. 2, but labelled as printer fluid droplets 118 in FIG. 1) ejected from printhead 102. Printhead 102 further includes an impedance sensor 104 positioned in firing chamber 106 to contact printer fluid to measure impedance values of the printer fluid. Impedance sensor 104 is connectable to a controller (not shown in FIG. 2, but labelled as controller 110 in FIG. 1) to transmit impedance values of printer fluid to the controller.

FIG. 3 is a diagram of an example system 100 including only printhead 102 and controller 110 connected via communication link 128. For convenience, system 100 of FIG. 3 includes the same reference numerals as that illustrated and described above with respect to system 100 of FIG. 1. Unlike the diagram of system 100 of FIG. 1, which is intended to depict a portion of a system ready for operation on site, the diagram of system 100 of FIG. 3 is intended to illustrate only a subset of components that might be included in a commercial product sold as a printhead system. For example, it is appreciated that some printhead systems are not sold along with printer fluid or printer fluid reservoirs. Moreover, it is appreciated that system 100 of FIG. 3 can include additional, fewer, or alternative components or functionality as system 100 of FIG. 1 and/or can be modified or assembled to include additional components, functionality, etc. Moreover, various aspects of system 100 of FIG. 1 can be incorporated into system 100 of FIG. 3 and vice versa. As an example, system 100 of FIG. 3 can include an ejector 112 positioned in a firing chamber to eject printer fluid droplets from printhead 102 (as shown for example in system 100 of FIG. 1). In addition, it is appreciated that printhead system 100 may include other aspects, such as various sensors, printer fluid lines, structural supports, etc. that are intentionally omitted in the simplified diagram of FIG. 3.

Similar to system 100 of FIG. 1, system 100 of FIG. 3 can include printhead 102 including firing chamber 106 to receive printer fluid (not shown in FIG. 3, but labelled as printer fluid 108 in FIG. 1), and nozzle 116 in fluid communication with firing chamber 106. Similar to nozzle 116 of system 100 of FIG. 1, nozzle 116 of printhead 102 of FIG. 3 can, for example, be designed to direct printer fluid droplets 118 (not shown in FIG. 3, but labelled as printer fluid droplets 118 in FIG. 1) ejected from printhead 102. Similar to printhead 102 of FIG. 1, printhead 102 of system 100 of FIG. 3 can include impedance sensor 104 positioned in firing chamber 106 to contact printer fluid to measure impedance values of the printer fluid.

System 100 can further include printhead controller 110 in data communication with impedance sensor 104. Printhead controller 110 can, for example, include memory resource 120 storing machine readable instructions 130 to cause a processing resource (not shown in FIG. 3, but labelled as processing resource 126 in FIG. 1) to receive impedance sensor values from impedance sensor 104. Printhead controller 110 can, for example, further include memory resource 120 storing machine readable instructions 130 to cause a processing resource (not shown in FIG. 3, but labelled as processing resource 126 in FIG. 1) to determine whether the received impedance sensor values correlate to the production of an effective drive bubble for printhead 102.

Figure 4:
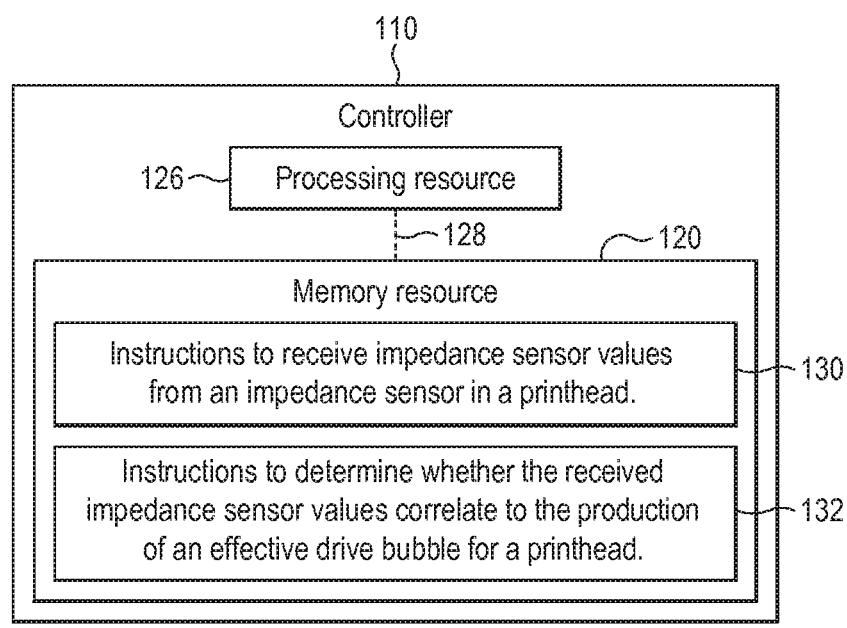
FIG. 4 is a diagram of a controller, according to an example.

FIG. 4 is a diagram of an example printhead controller 110 by itself. For convenience, controller 110 of FIG. 4 includes the same reference numerals as that illustrated and described above with respect to system 100 of FIG. 1. Unlike the diagram of system 100 of FIG. 1, which illustrates a complete system 100, the diagram of controller 110 of FIG. 4 is intended to illustrate only a subset of components that might be included in a commercial product sold as a printhead controller. For example, it is appreciated that some controllers are not sold along with printheads or printer fluid. Moreover, it is appreciated that system 100 of FIG. 4 can include additional, fewer, or alternative components or functionality as system 100 of FIG. 1 and/or can be modified or assembled to include additional components, functionality, etc. Moreover, various aspects of system 100 of FIG. 1 can be incorporated into controller 110 of FIG. 4 and vice versa. In addition, it is appreciated that controller 110 of FIG. 4 can include other components, such as power supplies, data ports, etc, that are intentionally omitted in the simplified diagram of FIG. 4.

Similar to system 100 of FIG. 1, controller 110 of FIG. 4 includes processing resource 126 and memory resource 120. Memory resource 120 stores machine readable instructions to cause the processor to receive impedance sensor values from an impedance sensor in a printhead (instructions 132). Instructions 132 of controller 110 of FIG. 4 can have similar functionality as instructions 322 of controller 130 of FIG. 1 described above but can include additional, alternative, or fewer aspects than instructions 122 of FIG. 1 described above. Memory resource 120 stores machine readable instructions to determine whether the received impedance sensor values correlate to the production of an effective drive bubble for the printhead (instructions 134). Instructions 134 of controller 110 of FIG. 4 can have similar functionality as instructions 124 of controller 110 of FIG. 1 described above but can include additional, alternative, or fewer aspects than instructions 124 of FIG. 1 described above.

Figure 5:
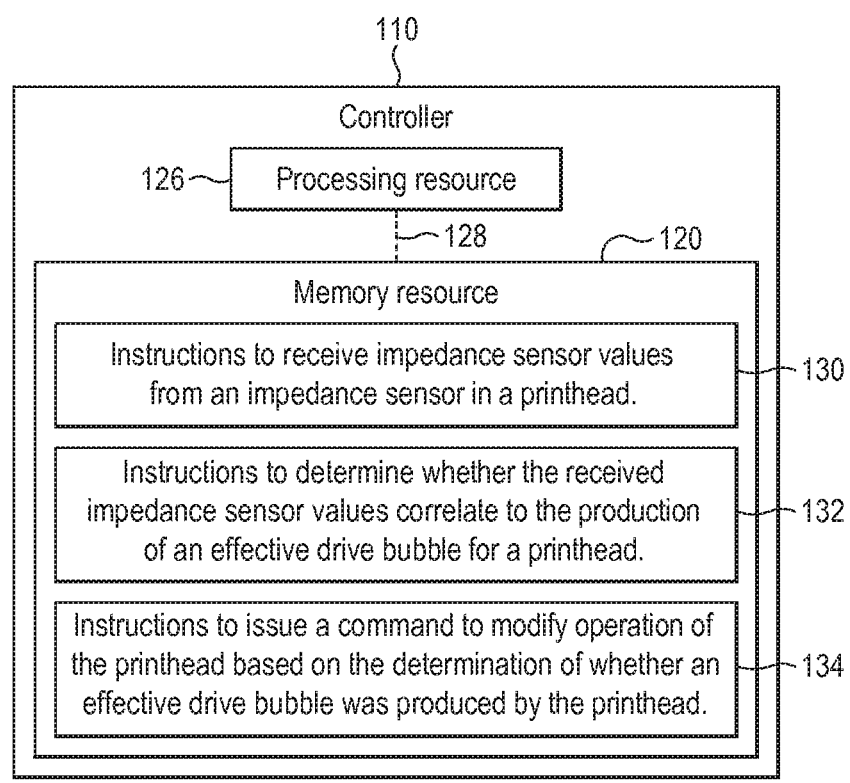
FIG. 5 is a diagram of a controller, according to another example.

FIG. 5 is a diagram of another example printhead controller 110 by itself. For convenience, controller 110 of FIG. 5 includes the same reference numerals as that illustrated and described above with respect to system 100 of FIG. 5. However, it is appreciated that controller 130 of FIG. 5 can include additional, fewer, or alternative components or functionality as controller 110 of FIG. 5 and/or can be modified or assembled to include additional components, functionality, etc. Like controller 110 of FIG. 5, controller 110 of FIG. 5 includes processing resource 126 and memory resource 120 storing instructions 132 and 134.

Controller 110 of FIG. 5 further includes instructions 334 to cause processing resource 126 to issue a command to modify operation of printhead 102 based on the received impedance sensor values. For example, in some implementations, firing parameters, such as power, voltage, pulse width, firing pulse, timing, etc., can be modified based on impedance sensor values. As an example, if impedance sensor values indicate that an effective drive bubble was not produced by printhead 102 using a first set of firing parameters, then controller 110 may issue a command to modify operation of printhead 102 by using a different set of firing parameters that are predicted to produce an effective drive bubble. It is appreciated that in some implementations, controller 110 can issue a command to modify operation of printhead 102 by communicating with a servicing station to indicate that a servicing (e.g., wiping) operation of printhead 102 should be performed. Commands to modify operation of printhead 102 can be time limited or can be open ended time-wise. For example, in some implementations, operation can be in the form of a permanent or semi-permanent change in the firing energy (e.g., defining a new baseline) or just a temporary change (e.g., to blast off material from nozzle 116).

Figure 6:
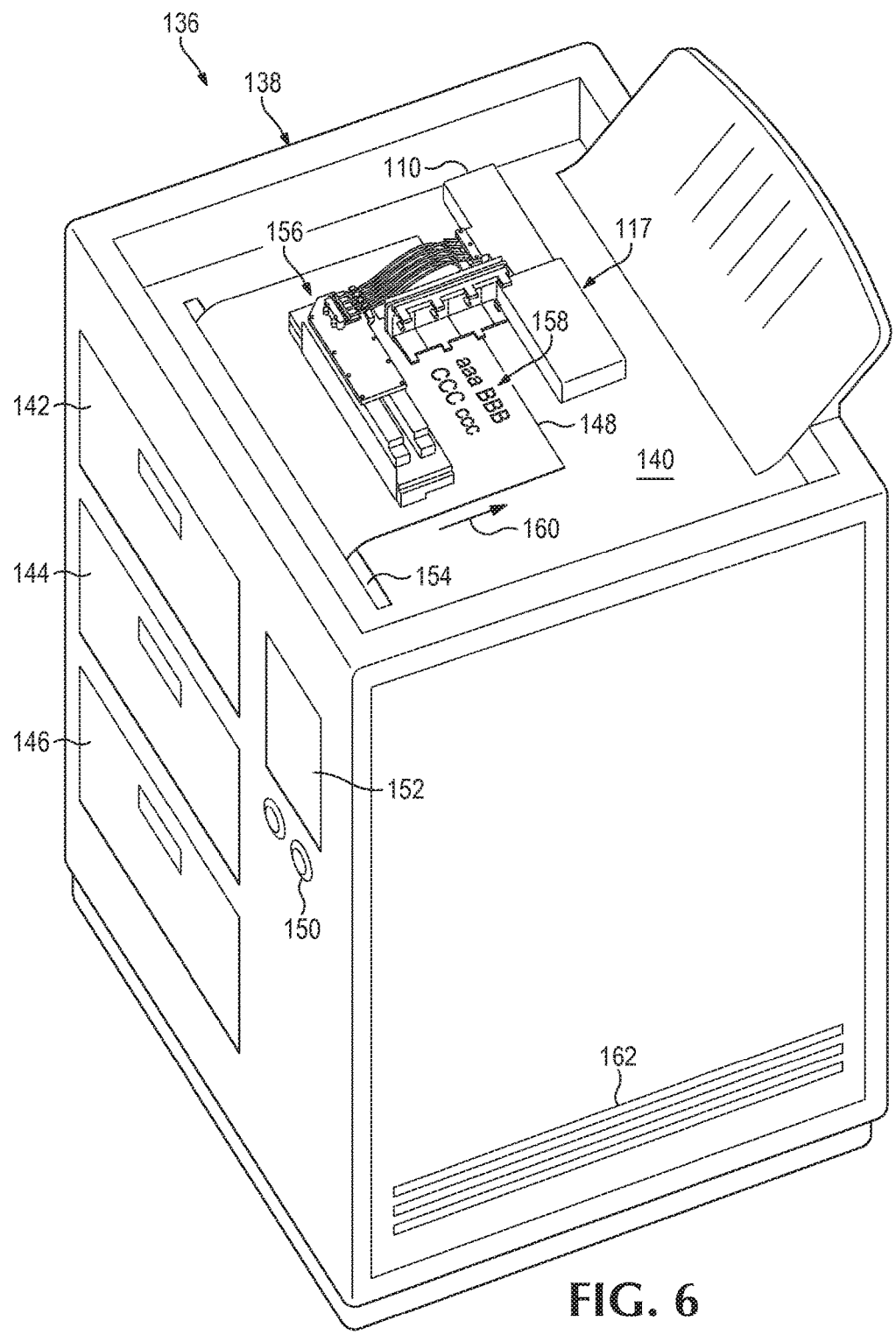
FIG. 6 is a diagram of a printer, according to an example.

FIG. 6 is a diagram of a printer 136 including a system 100 having an impedance sensor 104 to measure impedance values of printer fluid 108. For convenience, printer 136 of FIG. 5 includes the same reference numerals as that illustrated and described above with respect to system 100 of FIG. 1. Unlike the diagram of system 300 of FIG. 1, which is intended to depict a portion of a system ready for operation on site, the diagram of printer 136 of FIG. 5 is intended to illustrate only a subset of components that might be included in a commercial product sold as a printer. For example, it is appreciated that some printers are not sold along with printer fluid or printer fluid reservoirs. Moreover, it is appreciated that printer 136 of FIG. 5 can include additional, fewer, or alternative components or functionality as system 100 of FIG. 1 and/or can be modified or assembled to include additional components, functionality, etc. Moreover, various aspects of system 100 of FIG. 1 can be incorporated into printer 136 of FIG. 5 and vice versa. In addition, it is appreciated that printer 136 may include other aspects, such as various sensors, printer fluid lines, structural supports, etc. that are intentionally omitted in the simplified diagram of printer 136 of FIG. 5.

As described in further detail below, printer 136 includes a housing 138 that houses various internal parts of printer 136, a printing cavity 140 in which system 100 and other components are located, first, second, and third media trays 142, 144, and 146 for holding a printer media 148 (or a single printer medium 148), buttons 150 to allow user input for printer 136, and a display screen 152 to display information regarding printer 136. It is appreciated that, in some implementations, printer 136 may include additional, fewer, or alternative components. As but one example, in some implementations, printer 136 may not include buttons 150 or display screen 152 and may instead be remotely controlled by an external computer or controller.

In use, printer media 148 is passed through a slot 154 of printer 136 and is then positioned under a printer cartridge 156. Cartridge 156 includes an array of printheads 102 for ejecting printer fluid onto printer media 148. Each printhead can, for example, be fluidly connected to respective printer fluid tanks to receive printer fluid from each tank. System 100 is designed for use with a fixed position print bar with a substrate-wide array of nozzles 116. In such implementations, printer media 148 can, during printing, be moved under nozzles 116 of cartridge 156. Cartridge 156 can be designed to print text, pictures, or other graphics 158 onto printer media 148 by propelling droplets of liquid printing fluid onto printer media 148. For example, when the printhead is located at the desired width and length location, the printhead can be instructed to propel one or more droplets of printing fluid onto printer media 148 in order to print graphic 158 onto printer media 148. Printhead 102 and/or printer media 148 then be moved to another position and the printhead can be instructed to propel additional droplets of printing fluid onto printer media 148 in order to continue printing the graphic onto printer media 148.

Housing 138 of printer 136 is designed to house various internal parts of printer 136, such as system 100, a feeder module to feed printer media through printer 136 along feed direction 160, a processor for controlling operation of printer 136, a power supply for printer 136, and other internal components of printer 136. In some implementations, housing 138 can be formed from a single piece of material, such as metal or plastic sheeting. In some implementations, housing 138 can be formed by securing multiple panels or other structures to each other. For example, in some implementations, housing 138 is formed by attaching separate front, rear, top, bottom, and side panels. Housing 138 can include various openings, such as openings to allow media trays 142, 144, and 146 to be inserted into housing 138, as well as vents 162 to allow airflow into the interior of printer 136.

Media trays 142, 144, and 146 can be used to store printer media, such as for example printer paper. Each media tray can, for example, be designed to hold the same or a different size media. For example, media tray 142 can be designed to hold standard letter-sized paper, media tray 144 can be designed to hold A4 paper, and media tray 144 can be designed to hold 11×17 paper. It is appreciated that system 100 can be used in printers with only a single media tray or, in some implementations, with no media trays.

Printer 136 can include one or more input devices to send operator inputs to printer 136. For example, as depicted in FIG. 6, such input devices can include buttons 150, which can, for example, be designed to allow an operator to cancel, resume, or scroll through print jobs. Buttons 150 can also be designed to allow an operator to view or modify printer settings. It is appreciated that in some implementations, printer 136 can be remotely controlled by a remote computer or operator and may not include buttons 150 or other user inputs.

Printer 136 can include one or more output devices to provide output information from printer 136 to an operator. For example, as depicted in FIG. 6, such an output device can be in the form of a display screen 152 connected to a processor to display information regarding printer 136, such as information regarding a current or queued print job, information regarding settings of printer 136, or other information. It is appreciated that printer 136 may include other types of output devices to convey information regarding printer 136, such as a speaker or other suitable output device.

In some implementations, display screen 152 and buttons 150 can be combined into a single input/output unit. For example, in some implementations, display screen 152 can be in the form of a single touchscreen that both accepts input and displays output. In some implementations, printer 136 does not include any input/output units and is instead connected to another device or devices for receiving input and sending output. For example, in some implementations, printer 136 can interface with a remote computer over the internet or within an internal network. The remote computer can, for example, receive input from a keyboard or other suitable input device, and output information regarding printer 136 via a monitor or other suitable output device.

While certain implementations have been shown and described above, various changes in form and details may be made. For example, some features that have been described in relation to one implementation and/or process can be related to other implementations. In other words, processes, features, components, and/or properties described in relation to one implementation can be useful in other implementations. Furthermore, it should be appreciated that the systems and methods described herein can include various combinations and/or sub-combinations of the components and/or features of the different implementations described. Thus, features described with reference to one or more implementations can be combined with other implementations described herein. It is further appreciated that the choice of materials for the parts described herein can be informed by the requirements of mechanical properties, temperature sensitivity, moldability properties, or any other factor apparent to a person having ordinary skill in the art. For example, one more of the parts (or a portion of one of the parts) can be made from suitable plastics, metals, and/or other suitable materials.

The above discussion is meant to be illustrative of the principles and various implementations of the present disclosure. Numerous variations and modifications will become apparent to those skilled in the art once the above disclosure is fully appreciated. It is intended that the following claims be interpreted to embrace all such variations and modifications.

What is claimed is:
1. A printhead comprising:
a firing chamber to receive a printer fluid;
an ejector positioned in the firing chamber to eject the printer fluid droplets from the printhead;
a nozzle in fluid communication with the firing chamber, wherein the nozzle is to direct printer fluid droplets ejected from the printhead;
an impedance sensor positioned in the firing chamber to contact the printer fluid to measure impedance values of the printer fluid, wherein the impedance sensor is connectable to a controller to transmit the impedance values of the printer fluid to the controller; and a controller to modify firing parameters for the ejector based on the transmitted impedance values of the printer fluid.

2. The printhead of claim 1, wherein the impedance sensor is to measure the impedance values correlated to determine a state of a drive bubble of the printer fluid.

3. The printhead of claim 1, wherein the impedance sensor is to measure the impedance values correlated to determine a nucleation threshold state of a drive bubble of the printer fluid.

4. The printhead of claim 1, wherein the impedance sensor is to measure the impedance values correlated to determining whether an effective drive bubble has been created by the ejector.

5. The printhead of claim 1, wherein the ejector is in the form of a thermal ink jet resistor to heat the printer fluid droplets so as to eject printer fluid droplets from the printhead.

6. The printhead of claim 1, wherein the ejector is in the form of a piezo-electric actuator positioned in the firing chamber to eject the printer fluid droplets from the printhead.

7. The printhead of claim 1, wherein the impedance sensor is connectable to a controller to transmit the impedance values of the printer fluid to the controller in real-time.

8. The printhead of claim 1, wherein the impedance sensor is a first impedance sensor, and wherein the printhead further comprises:

a second impedance sensor positioned in the firing chamber to contact the printer fluid to measure the impedance values of the printer fluid, wherein the second impedance sensor is connectable to a controller to transmit the impedance values of the printer fluid to the controller.

9. The printhead of claim 1, further comprising an insulator disposed over the impedance sensor.

10. The printhead of claim 1, wherein:

the impedance sensor comprises two electrodes; and
one electrode of the impedance sensor is a common structure for impedance sensors of other printheads.

11. A printhead controller comprising:

a processing resource; and
a memory resource storing machine readable instructions to cause the processing resource to:
receive impedance sensor values from an impedance sensor in a printhead;
determine whether the received impedance sensor values correlate to the production of an effective drive bubble for the printhead; and
issue a command to modify firing parameters for the ejector based on the received the impedance sensor values.

12. The printhead controller of claim 11, wherein the memory stores machine readable instructions to cause the processor to:

trigger a printhead servicing operation for the printhead based on the received impedance sensor values.

13. The printhead controller of claim 11, wherein modifying firing parameters comprises modifying at least one element selected from the group consisting of:

firing power;
firing voltage;
firing pulse width; and
firing pulse timing.

14. The printhead controller of claim 11, wherein the memory stores machine readable instructions to cause the processor to identify various stages of drive bubble formation throughout a firing event.

15. The printhead controller of claim 11, wherein the memory stores machine readable instructions to cause the processor to determine properties of the printhead based on a type of bubble source.

16. A system comprising:

a printhead including:
a firing chamber to receive a printer fluid;
a nozzle in fluid communication with the firing chamber, wherein the nozzle is to direct printer fluid droplets ejected from the printhead; and
an impedance sensor positioned in the firing chamber to contact the printer fluid to measure the impedance values of the printer fluid; and
a printhead controller in data communication with the impedance sensor, the printhead controller including:
a memory resource storing machine readable instructions to cause a processing resource to:
receive the impedance sensor values from the impedance sensor;
determine whether the received impedance sensor values correlate to the production of an effective drive bubble for the printhead; and
issue a command to modify firing parameters for the ejector based on the received impedance sensor values.

17. The system of claim 16, wherein the instructions to determine whether the received impedance sensor values correlate to the production of an effective drive bubble for the printhead includes instructions to compare the received impedance values to data for effective drive bubble production for the same model of printhead for a specific type of printer fluid.

18. The system of claim 16, wherein the system includes multiple printheads with respective firing chambers, ejectors, impedance sensors, and nozzles to allow independent ejection of the printer fluid from different nozzles.

19. The printhead of claim 18, wherein each firing chamber of each printhead includes its own impedance sensor.

20. The system of claim 16, wherein the system comprises multiple printheads, a subset of which are printheads that include impedance sensors.

* * * * *